(12) United States Patent
Riestenberg et al.

(10) Patent No.: US 10,470,790 B2
(45) Date of Patent: Nov. 12, 2019

(54) SURGICAL INSTRUMENT WITH SELECTOR

(71) Applicant: Ethicon Endo-Surgery, LLC, Guaynabo, PR (US)

(72) Inventors: Paul F. Riestenberg, North Bend, OH (US); Benjamin M. Boyd, Fairborn, OH (US); Jacob S. Gee, Cincinnati, OH (US); Craig N. Faller, Batavia, OH (US); Charles J. Scheib, Loveland, OH (US); Thomas C. Gallmeyer, Ann Arbor, MI (US); Katelynn Kramer, Cincinnati, OH (US); Ryan M. Asher, Cincinnati, OH (US); Tylor C. Muhlenkamp, Cincinnati, OH (US); Geoffrey S. Strobl, Williamsburg, OH (US); David A. Monroe, Milford, OH (US)

(73) Assignee: Ethicon LLC, Guaynabo, PR (US)

( * ) Notice: Subject to any disclaimer, the term of this patent is extended or adjusted under 35 U.S.C. 154(b) by 501 days.

(21) Appl. No.: 14/970,778

(22) Filed: Dec. 16, 2015

(65) Prior Publication Data

US 2017/0172606 A1    Jun. 22, 2017

(51) Int. Cl.
*A61B 17/32* (2006.01)
*A61B 17/00* (2006.01)
*A61B 17/29* (2006.01)

(52) U.S. Cl.
CPC .......... *A61B 17/320092* (2013.01); *A61B 2017/0042* (2013.01); *A61B 2017/00115* (2013.01); *A61B 2017/00137* (2013.01); *A61B 2017/00181* (2013.01); *A61B 2017/00207* (2013.01); *A61B 2017/00367* (2013.01); *A61B 2017/00389* (2013.01); *A61B 2017/00407* (2013.01);

(Continued)

(58) Field of Classification Search
CPC ............ A61B 17/22004; A61B 17/225; A61B 17/320068; A61B 17/320092; A61B 2017/320094; A61F 9/00745
USPC .......................................... 606/169
See application file for complete search history.

(56) References Cited

U.S. PATENT DOCUMENTS 5,322,055 A   6/1994   Davison et al.
5,324,299 A   6/1994   Davison et al.
(Continued)

OTHER PUBLICATIONS

U.S. Appl. No. 61/410,603, filed Nov. 5, 2010.
International Search Report and Written Opinion dated Apr. 18, 2017 for Application No. PCT/US2016/066464, 11 pgs.

*Primary Examiner* — Melanie R Tyson
(74) *Attorney, Agent, or Firm* — Frost Brown Todd LLC

(57) ABSTRACT

An ultrasonic instrument includes a body, an actuation assembly, a shaft assembly, and an end effector. The actuation assembly includes a mode selection member and an activation member. The shaft assembly extends distally from the body. The shaft assembly includes an acoustic waveguide. The end effector includes an ultrasonic blade. The ultrasonic blade is in acoustic communication with the acoustic waveguide. The end effector is configured to be activated in a first activation mode in response to actuation of the activation member when the mode selection member is in a first position. The end effector is configured to be activated in a second activation mode in response to actuation of the activation member when the mode selection member is in a second position.

21 Claims, 14 Drawing Sheets

(52) U.S. Cl.
CPC . *A61B 2017/291* (2013.01); *A61B 2017/2946* (2013.01); *A61B 2017/320071* (2017.08); *A61B 2017/320094* (2017.08); *A61B 2017/320095* (2017.08)

(56) References Cited

U.S. PATENT DOCUMENTS

| | | | |
|---|---|---|---|
| 5,873,873 A | 2/1999 | Smith et al. | |
| 5,980,510 A | 11/1999 | Tsonton et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,423,082 B1 | 7/2002 | Houser et al. | |
| 6,773,444 B2 | 8/2004 | Messerly | |
| 6,783,524 B2 | 8/2004 | Anderson et al. | |
| 8,057,498 B2 | 11/2011 | Robertson | |
| 8,461,744 B2 | 6/2013 | Wiener et al. | |
| 8,591,536 B2 | 11/2013 | Robertson | |
| 8,623,027 B2 | 1/2014 | Price et al. | |
| 8,911,460 B2 | 12/2014 | Neurohr et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,572,592 B2 | 2/2017 | Price et al. | |
| 9,757,186 B2 | 9/2017 | Boudreaux et al. | |
| 2003/0216681 A1* | 11/2003 | Zhang | A61B 1/00135 604/22 |
| 2006/0079874 A1 | 4/2006 | Faller et al. | |
| 2007/0011713 A1 | 1/2007 | Abramson et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2012/0112687 A1 | 5/2012 | Houser et al. | |
| 2012/0116265 A1 | 5/2012 | Houser et al. | |
| 2013/0267975 A1* | 10/2013 | Timm | A61B 17/320068 606/169 |
| 2013/0303949 A1* | 11/2013 | Kawaguchi | A61B 17/282 601/2 |
| 2014/0005701 A1 | 1/2014 | Olson et al. | |
| 2014/0276770 A1* | 9/2014 | Ellman | A61B 18/1477 606/34 |
| 2015/0080924 A1 | 3/2015 | Stulen et al. | |
| 2015/0148834 A1* | 5/2015 | Gee | A61B 17/320068 606/169 |
| 2015/0313628 A1* | 11/2015 | Allen, IV | A61B 18/1445 606/171 |
| 2015/0313667 A1* | 11/2015 | Allen, IV | A61B 17/320092 606/51 |
| 2016/0175001 A1* | 6/2016 | Hibner | A61B 17/320092 606/28 |
| 2017/0172605 A1* | 6/2017 | Hibner | A61B 17/320068 |

\* cited by examiner

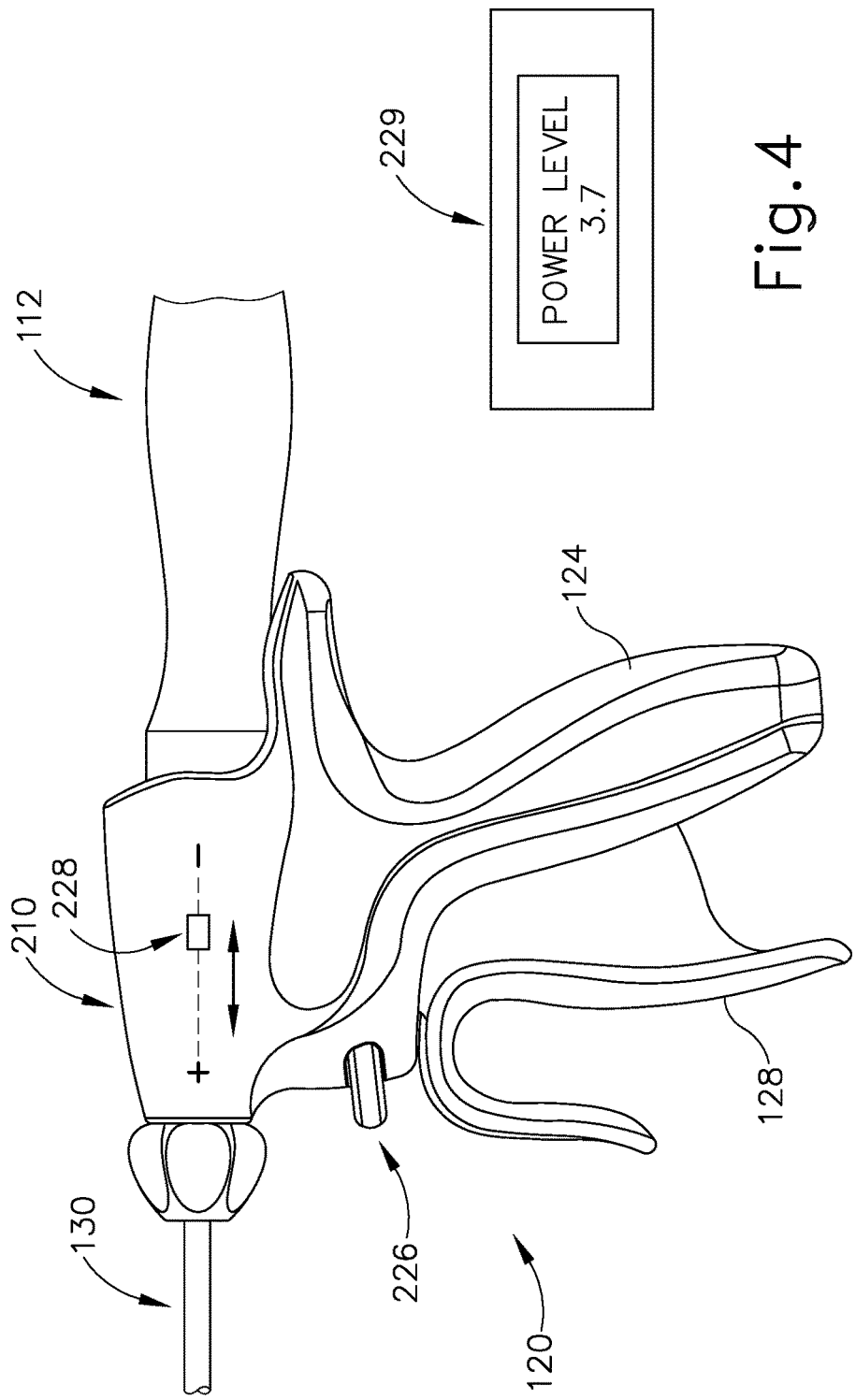

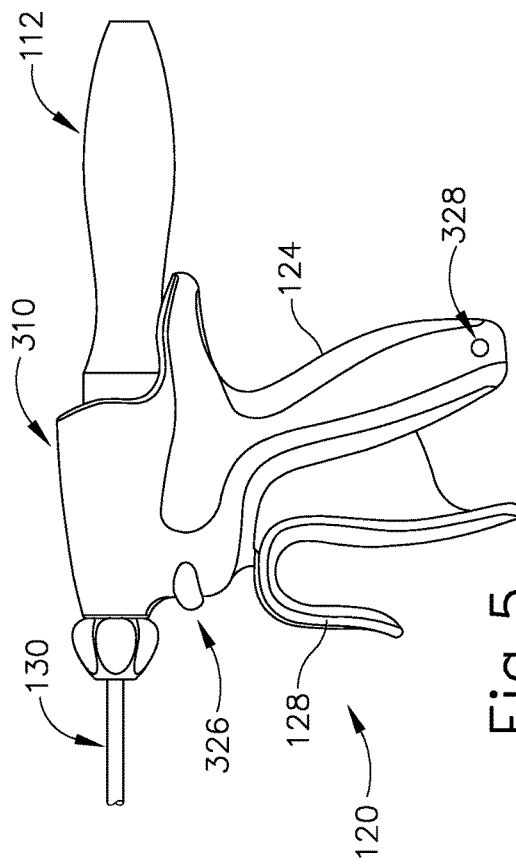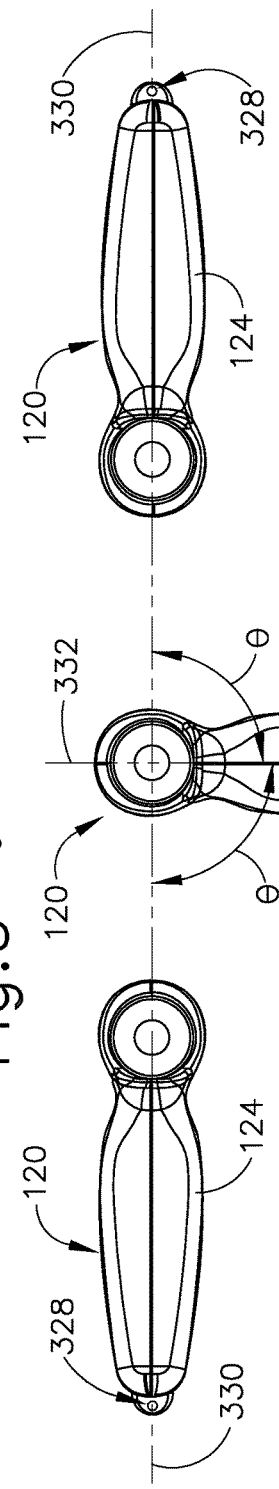

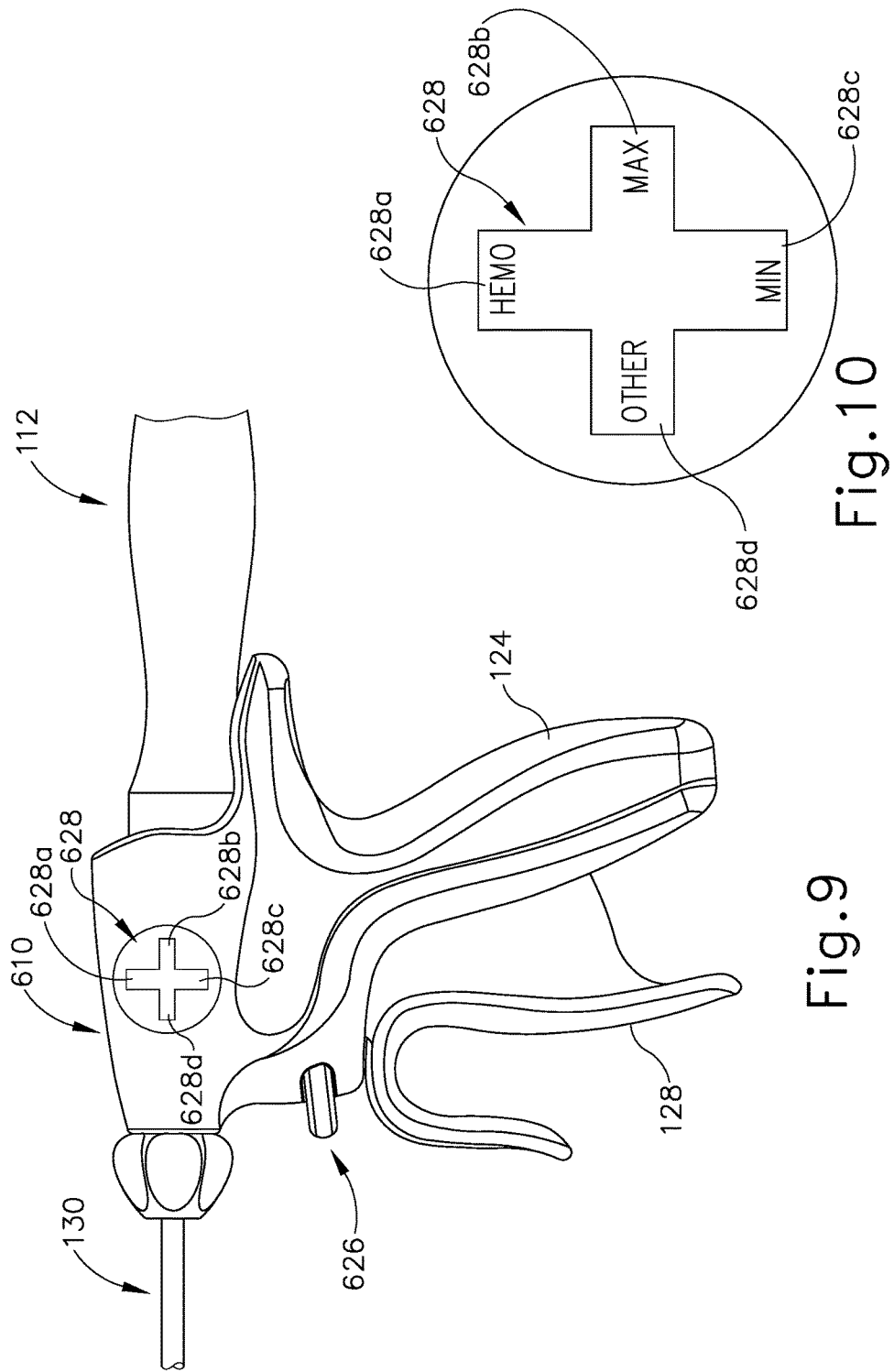

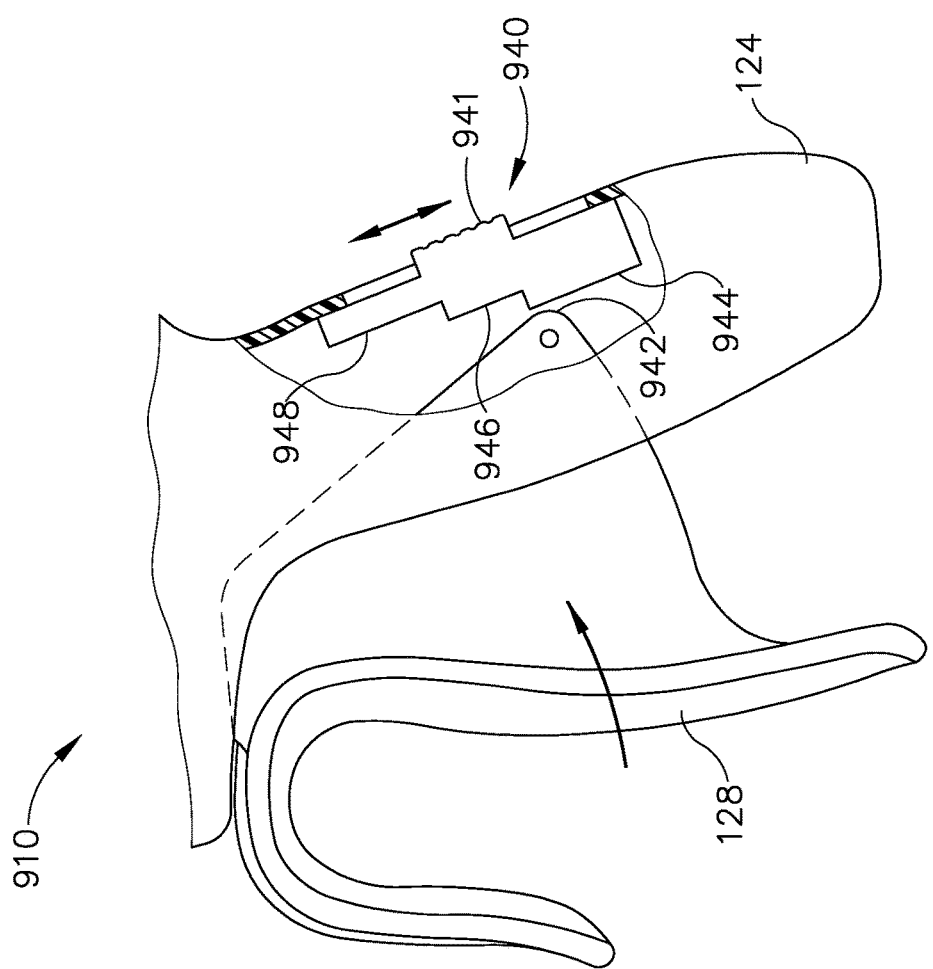

SURGICAL INSTRUMENT WITH SELECTOR

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460, on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3 depicts a side elevational view of another exemplary surgical instrument, including a power level selection feature;

FIG. 4 depicts a schematic view of a power display associated with the power level selection feature of FIG. 3;

FIG. 5 depicts a side elevational view of another exemplary surgical instrument, including a positional sensor;

FIG. 6A depicts a rear schematic view of a handle assembly of the instrument of FIG. 5, showing the handle assembly in a first position;

FIG. 6B depicts a rear schematic view of a handle assembly of the instrument of FIG. 5, showing the handle assembly in a second position;

FIG. 6C depicts a rear schematic view of a handle assembly of the instrument of FIG. 5, showing the handle assembly in a third position;

FIG. 9 depicts a side elevational view of another exemplary surgical instrument, including a multi-button switch feature for selecting an activation mode;

FIG. 10 depicts a detailed view of the multi-button switch feature of FIG. 9;

FIG. 14 depicts a side elevational view of an exemplary alternative handle assembly of another exemplary surgical instrument, showing another exemplary alternative blocking mechanism in a first position and a trigger in a non-actuated position;

Figure 1:
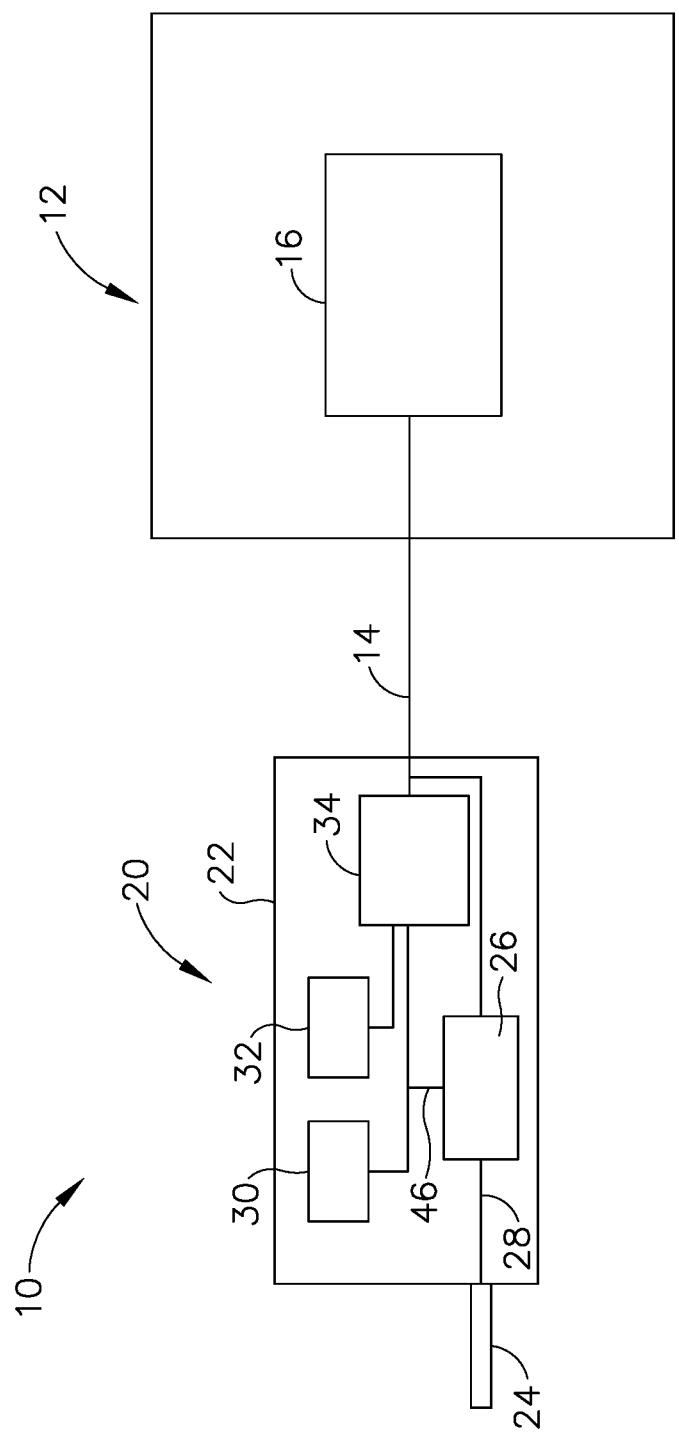
FIG. 1 depicts a block schematic view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers to the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations for instrument (20). It should be understood that the various examples of instrument (20) described below may be readily incorporated into a surgical system (10) as described above. It should also be understood that the various components and operability of instrument (20) described above may be readily incorporated into the exemplary versions of instrument (110) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
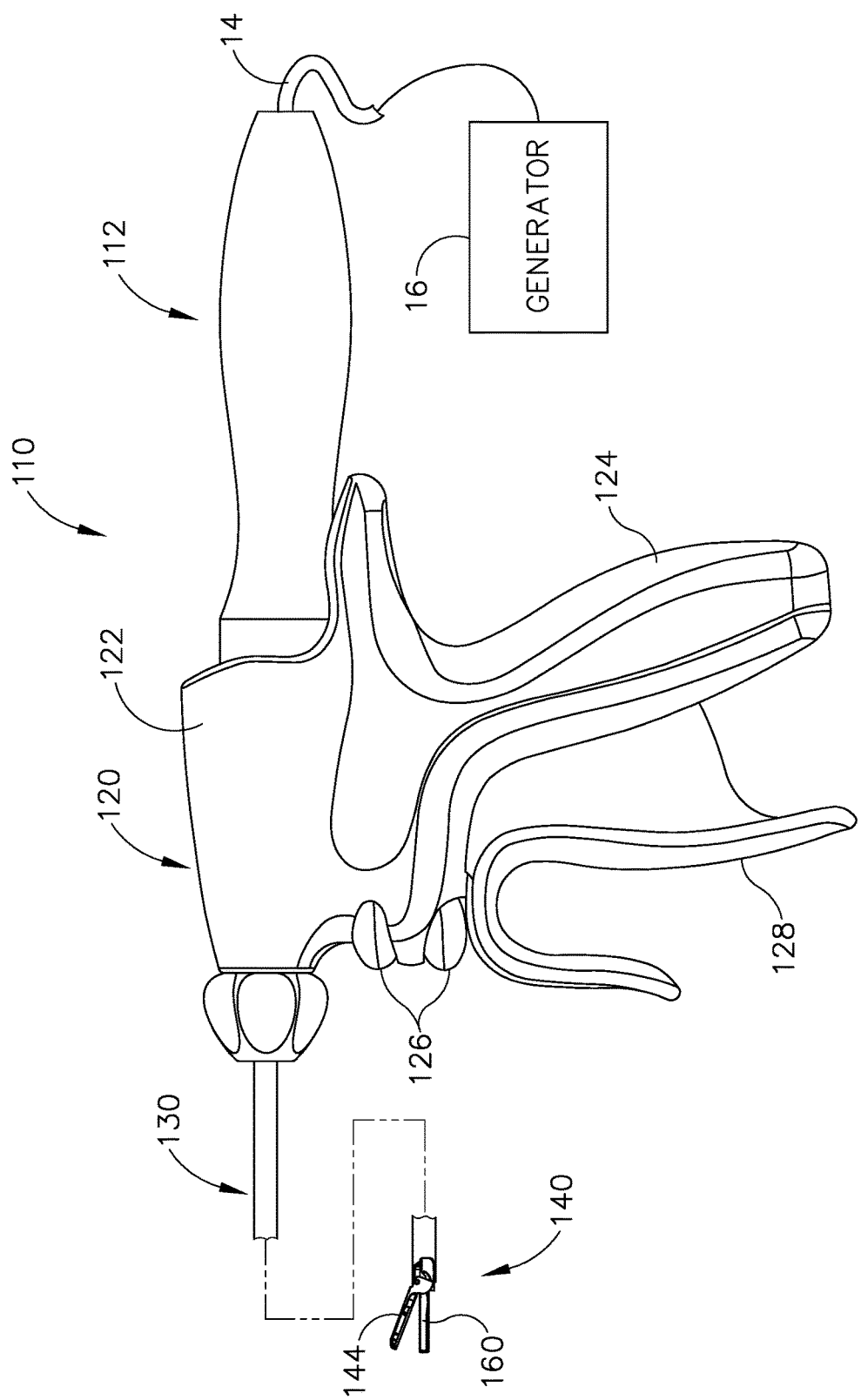
FIG. 2 depicts a side elevational view of another exemplary surgical instrument.

FIG. 2 illustrates an exemplary ultrasonic surgical instrument (110). At least part of instrument (110) may be constructed and operable in accordance with at least some of the teachings of U.S. Pat. Nos. 5,322,055; 5,873,873; 5,980,510; 6,325,811; 6,773,444; 6,783,524; 8,461,744; U.S. Pub. No. 2009/0105750, issued as U.S. Pat. No. 8,623,027 on Jan. 7, 2014; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pat. Pub. No. 2014/0114334, issued as U.S. Pat. No. 9,095,367 on Aug. 4, 2015; U.S. patent application Ser. No. 14/028,717, issued as U.S. Pat. No. 10,172,636 on Jan. 8, 2019; and/or U.S. Pat. App. No. 61/410,603. The disclosures of each of the foregoing patents, publications, and applications are incorporated by reference herein. As described therein and as will be described in greater detail below, instrument (120) is operable to cut tissue and seal or weld tissue substantially simultaneously. It should also be understood that instrument (120) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (120) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (120), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (110) of the present example comprises a handle assembly (120), a shaft assembly (130), and an end effector (140). Handle assembly (120) comprises a body (22) including a pistol grip (124) and a pair of buttons (126). Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Ultrasonic blade (160) may be configured and operable just like ultrasonic blade (24) described above.

Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Clamp arm (144) is thus operable to cooperate with ultrasonic blade (160) to grasp and release tissue; and clamp arm (144) is further operable to compress tissue against ultrasonic blade (160) to thereby enhance the communication of ultrasonic vibration from ultrasonic blade (160) to the tissue. Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 2.

An ultrasonic transducer assembly (112) extends proximally from body (122) of handle assembly (120). Transducer assembly (112) may be configured and operable just like transducer (26) described above. Transducer assembly (112) is coupled with a generator (116) via a cable (114). It should be understood that transducer assembly (112) receives electrical power from generator (116) and converts that power into ultrasonic vibrations through piezoelectric principles. Generator (116) may be configured and operable like generator (12) described above. Generator (116) may thus include a power source and control module that is configured to provide a power profile to transducer assembly (112) that is particularly suited for the generation of ultrasonic vibrations through transducer assembly (112). It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

As shown in FIG. 2, by way of example, one of the buttons (126) may be associated with a "seal" mode, such that actuating the particular one of the buttons (126) only seals tissue, but does not cut tissue, when the tissue is being clamped between clamp arm (144) and blade (160). In particular, activation of a first one of the buttons (136) may cause vibration of ultrasonic blade (160) at a relatively low amplitude. Similarly, by way of further example, the other of the buttons (126) may be associated with a "cut and seal" mode such that actuating the particular one of the buttons (126) may seal and cut tissue when the tissue is being clamped between clamp arm (44) and blade (160). In particular, activation of a second one of the buttons (136) may cause vibration of ultrasonic blade (160) at a relatively high amplitude. Other suitable operational modes that may be associated with buttons (126) will be apparent to persons skilled in the art in view of the teachings herein.

III. Ultrasonic Surgical Instrument with Alternative Power Level Selection Features In some instances it may be advantageous to include a variety of functionalities in a single surgical instrument. For example, when using ultrasonic surgical instruments, it may be useful in some instances to deliver varying levels of power or energy to tissue. Particularly, some instances may call for both cutting and sealing of tissue, but other instances may call for only sealing of tissue. Levels of energy and/or power that may be applied in a "seal" mode and in a "cut and seal" mode will be apparent to persons skilled in the art in view of the teachings herein. An operator may wish to select a "seal" mode when the operator wishes to seal tissue without cutting the tissue. An operator may wish to select a "cut and seal" mode when the operator wishes to cut and seal the tissue. While increasing the functionality of a surgical instrument to operate in a variety of modes may be advantageous, doing so may lead to an increased number of buttons, switches, and other control mechanisms that an operator must understand and utilize. Therefore, it is desirable to provide increased functionality of surgical instruments without increasing the complexity of use. The following examples provide enhanced control of power modes in variations of instrument (20, 110), without providing an unduly complex user interface.

A. Ultrasonic Instrument with Slidable Switch for Adjusting Activation Levels

FIG. 3 shows an exemplary alternative surgical instrument (210) that is configured to operate substantially similar to surgical instrument (110). Therefore, identical or similar structures are labeled with like reference numerals without further explanation below. It will be understood that although an end effector is not shown in FIG. 3, instrument (210) includes an end effector that is just like end effector (140). It will be further understood that transducer (112) may be in communication with a generator (12, 116) via cable (14). Surgical instrument (210) of this example includes a single activation button (226) and a slidable switch (228). As discussed in detail below, instrument (210) is configured to operate at different activation levels, depending on the position of switch (228), upon the actuation of activation button (226).

In the present example, switch (228) is slidable in the distal direction in order to increase the activation or power level of transducer (112) and blade (160) that will result from actuation of activation button (226). Similarly, switch (228) is slidable in the proximal direction to decrease the activation or power level of transducer (112) and blade (160) that will result from actuation of activation button (226). However, it will be understood that the relative sliding directions that result in an increase or decrease in the power level of transducer (112) may be reversed. In the present example, switch (228) is associated with a potentiometer that increases or decreases the power level linearly and continuously as switch (228) is moved distal or proximal directions, respectively.

In the example shown, switch (228) enables transducer (112) and blade (160) to operate across a continuum of modes (e.g., power levels) without being constrained to discrete settings (maximum, minimum, etc.). As shown in FIG. 4, the power level is displayed on a display (229) of a generator, such as generator (12, 116), in one-tenth increments between "0.0" and "5.0." However, the power level may be displayed in any other suitable ways that will be apparent to persons skilled in the art in view of the teachings herein. In some examples, when switch (226) is in the proximal-most position, actuation of button (226) may not result in activation of transducer (112) and blade (160). Thus, in such examples, switch (228) in the proximal-most position may be considered to be in an "off" position. However, in other examples, the proximal-most position of switch (228) may not be associated with an "off" or "zero" setting; and may instead be associated with a "minimum" power level/activation mode, for example, while the distal most position that switch (228) may reach may be associated with a "maximum" power level/activation mode.

In some examples, certain positions of the switch (228) may be associated with the "seal" and/or "cut and seal" activation modes, which may or may not be different than the "minimum" and maximum" activation modes. In such examples, instrument (210) may include appropriate labels indicating to a user which positions of switch (228) are associated with particular activation modes of transducer (112). In alternative examples, rather than enabling transducer (112) and blade (160) to operate among a continuum of modes, switch (228) may enable transducer (112) to operate in multiple discrete modes, such as any of the activation modes described herein. Other suitable configurations of switch (228) and activation modes according to the positioning of switch (226) will be apparent to persons skilled in the art in view of the teachings herein.

While switch (228) is configured to translate along a path that is parallel to the longitudinal axis of shaft assembly (132) in this example, switch (228) may instead be configured to translate along a path that is perpendicular to or obliquely angled relative to the longitudinal axis of shaft assembly (132).

B. Ultrasonic Instrument with Sensor for Detecting Positional Characteristics of Instrument FIGS. 5-6C show an exemplary alternative surgical instrument (310) that is configured to operate substantially similar to surgical instrument (110). Therefore, identical or similar structures are labeled with like reference numerals without further explanation below. It will be understood that although an end effector is not shown in FIG. 5, instrument (310) includes an end effector that is just like end effector (140). It will be further understood that transducer (112) may be in communication with a generator (12, 116) via cable (14). Surgical instrument (310) includes a single activation button (326) and is configured to activate transducer (112) and blade (160) in different activation modes depending on the orientation of handle assembly (120).

In the present example, handle assembly (120) includes a sensor (328) that is configured to sense the orientation of handle assembly (120) and thereby select the activation mode of transducer (112) and blade (160) depending on the orientation of handle assembly (120). In the example shown, sensor (328) comprises an accelerometer. However, in other examples, sensor (328) may comprise any other elements that are capable of sensing or detecting the orientation of handle assembly (120). As shown, sensor (328) is positioned in pistol grip (124) of handle assembly (120). However, sensor (328) may be positioned in any other suitable portions of instrument (310). It should also be understood that more than one sensor (328) may be used to sense the orientation of instrument (310).

In the present example, transducer (112) and blade (160) may be activated in a first activation mode or power level when handle assembly (120) is in a first orientation (FIG. 6A) and in a second activation mode or power level when handle assembly (120) is in the second and third positions (FIGS. 6B and 6C, respectively). Thus, sensor (328) essentially acts as a switch that enables the activation modes or power levels of instrument (310) to be changed, but without requiring the operator to press a button or otherwise manually actuate a switch. In other words, the operator may select the activation mode or power level simply by re-orienting handle assembly (120) among the orientations shown in FIGS. 6A-6C.

The views provided in FIGS. 6A-6C are provided from the perspective of an operator located at the proximal end of instrument (310), viewing distally toward instrument (310). It should be understood during the following discussion that sensor (328) is operable to detect the orientations described below, enabling instrument (310) to provide different functionality based on the sensed orientation of handle assembly (120). In the first orientation as shown in FIG. 6B, pistol grip (124) extends along a first plane (330). In the example shown, first plane (330) is horizontal such that first plane (330) is parallel to the ground. In an actual use setting, pistol grip (124) is pointing to the left relative to the operator when instrument (310) is in the first orientation. It should be understood that even in settings where pistol grip (124) is pointing to the left relative to the operator, pistol grip (124) might not necessarily be parallel to the ground.

In the second orientation, pistol grip (124) extends along a second plane (332) that is positioned at an angle ($\theta$) relative to first plane (330). In the present example, angle ($\theta$) is approximately 90°, though it should be understood that planes (330, 332) may have any other suitable angular relationship with each other. In the example shown, second plane (332) is vertical such that second plane (332) is perpendicular to the ground. In an actual use setting, pistol grip (124) is pointing toward the operator when instrument (310) is in the second orientation. It should be understood that even in settings where pistol grip (124) is pointing toward the operator, pistol grip (124) might not necessarily be perpendicular to the ground.

In the third orientation, pistol grip (124) extends along first plane (330) again. However, in the third orientation, pistol grip (124) is pointing to the right relative to the operator when instrument (310) is in the second orientation. In the present example, the first and third orientations are each angularly offset from the second orientation by the angle ($\theta$) of 90°; and the first and third orientations are each angularly offset from each other by an angle of 180°. In some other versions, the first and third orientations are each angularly offset from the second orientation by some other angle ($\theta$). It should also be understood that the first orientation may be offset from the second orientation by an angle that differs from the angle defining an angular offset between the second and third orientation. For example, it will be understood that a person may pronate or supinate their hand at different angles depending on the initial angular position of the hand. In some examples, therefore, sensor (328) may be able to accommodate for such limitations to vary the values of $\theta_2$ and $\theta_3$. Further, to accommodate for operators with different handedness (i.e., left and right), sensor (328) (or another sensor) may be operable to detect the handedness of the operator and may alter the angle ($\theta$) based on such information.

In some versions, instrument (310) provides a first activation mode when handle assembly (120) is at the first orientation; a second activation mode when handle assembly (120) is at the second orientation; and a third activation mode when handle assembly (120) is at the third orientation. In some other versions, instrument (310) provides a first activation mode when handle assembly (120) is at the first orientation; a second activation mode when handle assembly (120) is at either the second orientation or the third orientation. By way of example only, a first activation mode may be associated with the "seal" activation mode described herein, while the second activation mode may be associated with the "cut and seal" activation mode described herein. In other examples, however, the first and second activation modes may be associated with other activations modes or power levels described herein; or with other suitable activation modes as will be apparent to those of ordinary skill in the art in view of the teachings herein.

C. Ultrasonic Instrument with Toggle Button for Selecting Among Operating Modes

Figure 7:
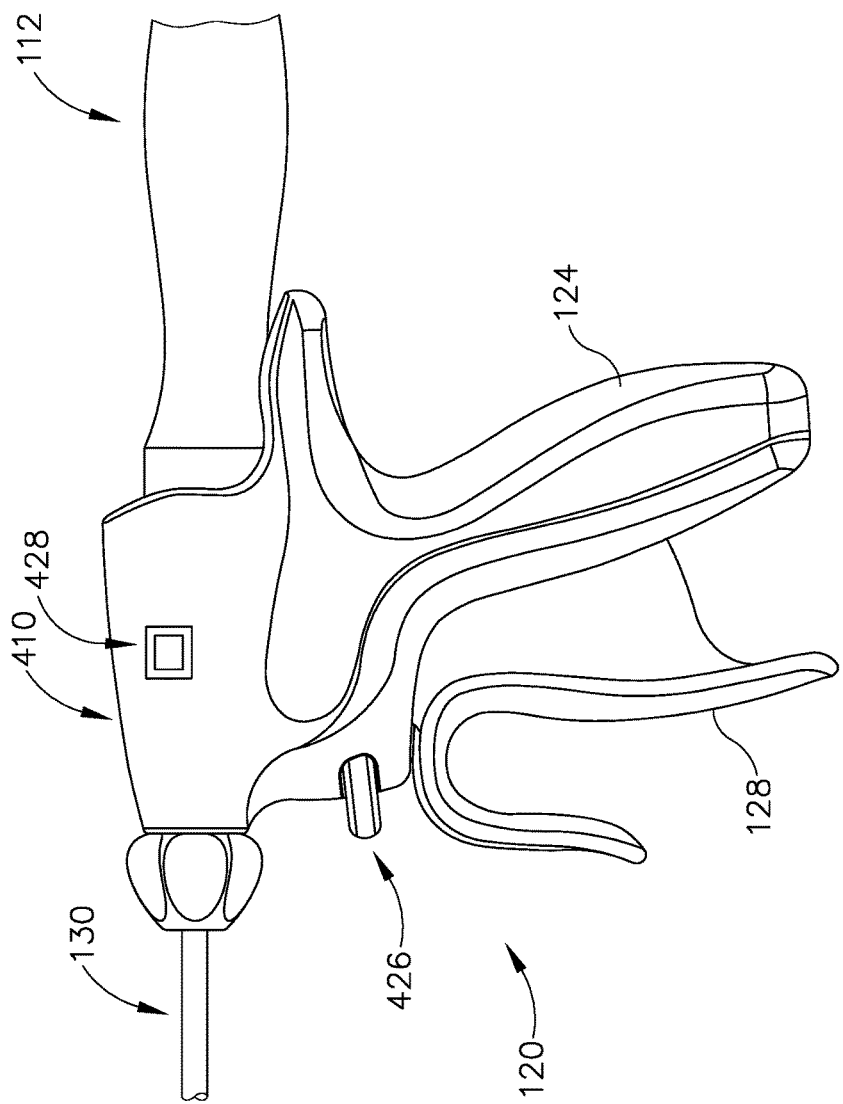
FIG. 7 depicts a side elevational view of another exemplary surgical instrument, including a toggle switch for selecting an activation mode.

FIG. 7 shows an exemplary alternative surgical instrument (410) that is configured to operate substantially similar to surgical instrument (110). Therefore, identical or similar structures are labeled with like reference numerals without further explanation below. It will be understood that although an end effector is not shown in FIG. 7, instrument (410) includes an end effector that is just like end effector (140). It will be further understood that transducer (112) may be in communication with a generator (12, 116) via cable (14). Surgical instrument (410) includes a single activation button (426) and a selector switch (428) that may be actuated to select a power level or activation mode. Therefore, as discussed in detail below, instrument (410) is configured to activate transducer (112) and blade (160) at different operating modes or power levels, depending on the mode selected by actuation of switch (428), and upon the actuation of activation button (426).

In the present example, switch (428) comprises a toggle button that is movable among a number of positions that are associated with particular activation modes. For example, switch (428) may be toggled between proximal and distal positions to thereby change the operation mode. As another merely illustrative example, switch (428) may comprise a button that is pressed repeatedly to toggle switch (428) between a non-depressed state and a fully depressed state. Some such versions may also provide a partially depressed state that switch (428) mat be toggled to. By way of example only, actuating switch (428) a first time may increase the power level from zero to a power level associated with the "seal" activation mode described above. Actuating switch (428) a subsequent time may increase the power level to a power level associated with the "cut and seal" activation mode described above; or to any suitable number of modes between zero and "seal," between "seal" and "cut and seal," and above "cut and seal." Instrument (410) may be switchable among any suitable number of activation modes. In some examples, switch (428) is associated with a detent mechanism that maintains the position of switch (428) in a particular position each time switch (428) is pressed.

In some variations, switch (428) comprises a rotary scroll wheel. In such examples, switch may (428) be associated with a potentiometer that increases or decreases the power level linearly and continuously as switch (428) is rotated in the first or second directions, respectively. In some examples, however, rotation of switch (428) may result in step-wise increasing or decreasing among discrete power levels or operation modes. For example, rotation of switch (428) in the first direction may incrementally increase the power level from zero, to a power level associated with the "seal" activation mode described above, to a power level associated with the "cut and seal" activation mode described above, and any suitable number of modes between zero and "seal," between "seal" and "cut and seal," and above "cut and seal." Similarly, rotation of switch (428) in the second direction may incrementally decrease the power level from, for example, the power level associated with the "cut and seal" activation mode, to the "seal" activation mode, and to zero, and any suitable number of modes between "cut and seal" and "seal," and between "seal" and zero. Other suitable activation modes according to the positioning of switch (428) will be apparent to persons skilled in the art in view of the teachings herein.

As shown, switch (428) is positioned on only one side of the handle assembly (120). In some other examples, switch (428) may be positioned on the other side of handle assembly (120) not shown. In still other examples, there may be a switch (428) on each side of the handle assembly (120) in order to accommodate for operators of different handedness. In the present example, switch (428) is in a position accessible by the thumb of the hand that grasps pistol grip (124). In other examples, switch (428) may be in other suitable positions that will be apparent to persons skilled in the art in view of the teachings herein.

Figure 8:
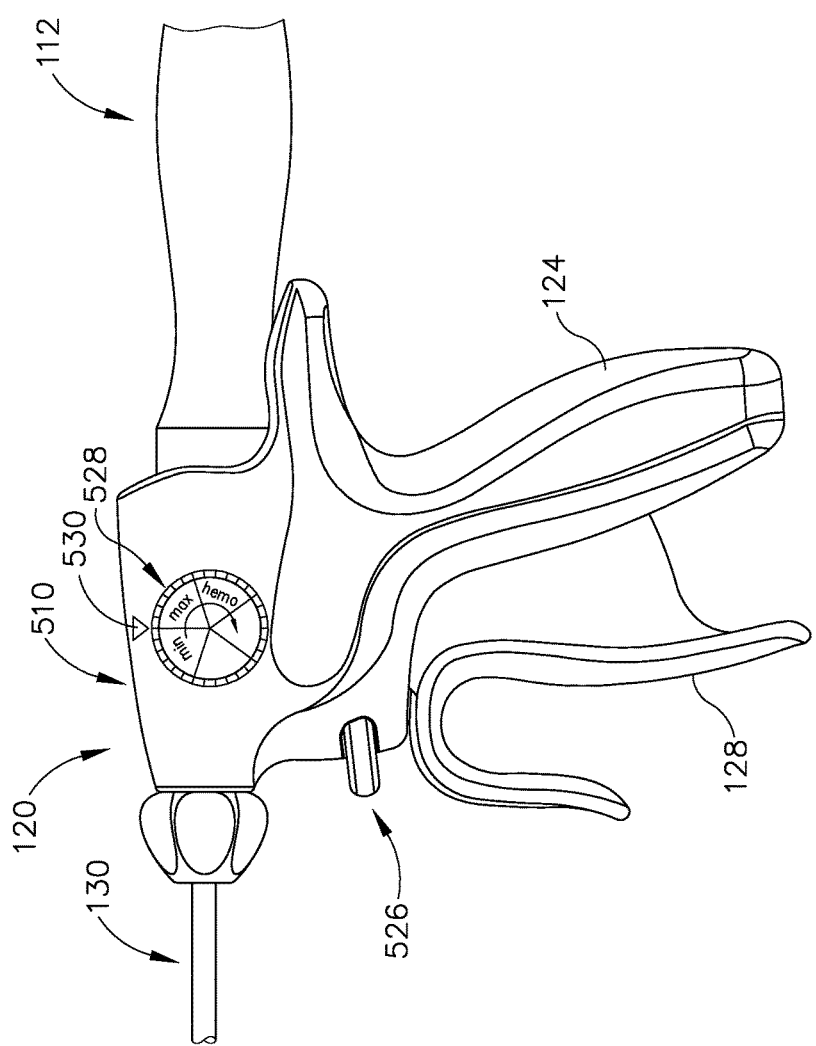
FIG. 8 depicts a side elevational view of another exemplary surgical instrument, including a rotary dial feature for selecting an activation mode.

D. Ultrasonic Instrument with Rotary Dial Feature for Selecting an Activation Mode FIG. 8 shows an exemplary alternative surgical instrument (510) that is configured to operate substantially similar to surgical instrument (110). Therefore, identical or similar structures are labeled with like reference numerals without further explanation below. It will be understood that although an end effector is not shown in FIG. 8, instrument (510) includes an end effector that is just like end effector (140). It will be further understood that transducer (112) may be in communication with a generator (12, 116) via cable (14). Surgical instrument (510) includes a single activation button (526) and a rotary dial feature (528) that may be rotated to select amongst various power levels or activation modes. Therefore, as discussed in detail below, instrument (510) is configured to activate transducer (112) and blade (160) at different operating modes or power levels, depending on the mode selected by rotation of dial (528), and upon the actuation of activation button (526).

In the example shown, rotation of dial (528) may result in step-wise increasing or decreasing among discrete power levels or operation modes. As shown, dial (428) is movable among a "MAX" (maximum) setting, a "MIN" (minimum) setting, and a "HEMO" (hemostasis) setting. Handle assembly (120) includes an arrow (530) that indicates to a user in which activation mode instrument (510) is currently set according to which portion of dial (528) is aligned with arrow (530). Levels of energy and/or power that may be applied in the "minimum," "maximum," "hemostasis," "seal" and "cut and seal" modes will be apparent to persons skilled in the art in view of the teachings herein. In some examples, dial (528) may be able to assume positions associated with other operating modes, such as the "seal" and "cut and seal" operating modes discussed herein. Other suitable activation modes according to the positioning of dial (528) will be apparent to persons skilled in the art in view of the teachings herein.

As shown, dial (528) is positioned on only one side of the handle assembly (120). In other examples, dial (528) may be positioned on the other side of handle assembly (120). In still other examples, there may be a dial (528) on each side of the handle assembly (120) in order to accommodate for operators of different handedness. In the present example, dial (528) is in a position that is accessible by the thumb of the hand grasping pistol grip (124). In other examples, dial (528) may be in other suitable positions that will be apparent to persons skilled in the art in view of the teachings herein.

E. Ultrasonic Instrument with Multi-Switch Button for Selecting Activation Mode

FIGS. 9-10 show an exemplary alternative surgical instrument (610) that is configured to operate substantially similar to surgical instrument (110). Therefore, identical or similar structures are labeled with like reference numerals without further explanation below. It will be understood that although an end effector is not shown in FIG. 9, instrument (610) includes an end effector that is just like end effector (140). It will be further understood that transducer (112) may be in communication with a generator (12, 116) via cable (14). As shown, instrument (610) includes a single activation button (626) and a button (628) having a plurality of switches associated with various operating modes. Therefore, as discussed in detail below, instrument (610) is configured to activate transducer (112) and blade (160) at different operating modes or power levels, depending on the mode selected by actuation of button (628), and upon the actuation of activation button (626).

In the present example, button (628) includes a first switch (628a), second switch (628b), third switch (628c), and fourth switch (628d). Actuation of one of switches (628a, 628b, 628c, 628d) changes the mode under which instrument (610) operates, upon actuation of activation button (626). As shown best in FIG. 10, first switch (628a) is associated with a "HEMO" (hemostasis) setting, second switch (628b) is associated with a "MAX" (maximum) setting, third switch (628c) is associated with a "MIN" (minimum) setting, and fourth switch (628d) is associated with an "OTHER" setting. Button (628) in some examples may include switches associated with additional or alternative operating modes, such as the "seal" and "cut and seal" operating modes discussed herein. Other suitable activation modes that may be selectable using switches (628a, 628b, 628c, 628d) will be apparent to persons skilled in the art in view of the teachings herein. Levels of energy and/or power that may be applied in the "minimum," "maximum," "hemostasis," "seal," and "cut and seal" modes will also be apparent to persons skilled in the art in view of the teachings herein.

As shown, button (628) is shaped like a "+" sign and includes four switches (628a, 628b, 628c, 628d) that allow for four operating modes. However, in other examples, button (628) may have any other suitable configuration and may include any suitable number of switches associated with any suitable number of operating modes. In the present example, button (628) extends along a plane that is parallel to the longitudinal axis of shaft assembly (130). In other versions, button (628) may extend along a plane that is oriented obliquely or perpendicularly relative to the longitudinal axis of shaft assembly (130).

As shown in the example of FIGS. 9-10, each switch (628a, 628b, 628c, 628d) is positioned on the same button (628). However, in some other examples, each switch (628a, 628b, 628c, 628d) may be positioned on a discrete, separate button. In some examples, there may be multiple switches associated with a single operating mode (e.g., such that there is a greater number of switches than possible operating modes), such as any of the operating modes discussed herein or any other operating modes that will be apparent to persons skilled in the art in view of the teachings herein. In still other examples, instrument (610) may include any number of switches associated with an equal number of operating modes. Further, in some examples, instrument (610) may include multiple buttons or switches, but may be capable of operating in only operating mode, such that each of the buttons or switches activates the same operating mode. Other suitable configurations of buttons and switches and operating modes associated therewith will be apparent to persons skilled in the art in view of the teachings herein.

IV. Ultrasonic Surgical Instrument with Mode Selection Through Closure Restriction The examples described above provide variation in operational modes by varying the power delivered to tissue through blade (160). It should also be understood that operational modes may be varied by varying the degree to which clamp arm (144) compresses tissue against blade (160). In particular, when clamp arm (144) compresses tissue against blade (160) with a relatively low amount of pressure, end effector (140) may provide a "seal only" mode, such that end effector (140) seals tissue relatively well but does not cut tissue relatively well. By contrast, when clamp arm (144) compresses tissue against blade (160) with a relatively high amount of pressure, end effector (140) may provide a "seal and cut" mode, such that end effector (140) cuts and seals tissue relatively well. As will be described below, instrument (110) may be modified to selectively restrict the degree to which clamp arm (144) may compress tissue against blade (160). For instance, instrument (110) may be modified to prevent clamp arm (144) from pivoting to a distance where clamp arm (144) would contact blade (160), since contact between clamp arm (144) and blade (160) would indicate tissue cutting. This may in turn provide selection between a "seal only" mode and a "seal and cut" mode of operation.

It may also be desirable to provide activation of transducer (112) and blade (160) in response to pivotal movement of trigger (128) toward pistol grip (124), without requiring the operator to separately actuate a button (126) to activate transducer (112) and blade (160). Various ways in which transducer (112) and blade (160) may be activated in response to pivotal movement of trigger (128) toward pistol grip (124) will be described in greater detail below.

FIGS. 11A-12C show an exemplary alternative surgical instrument (710) that is configured to operate substantially similar to surgical instrument (110). Therefore, identical or similar structures are labeled with like reference numerals without further explanation below. It will be further understood that transducer (112) may be in communication with a generator (12, 116) via cable (14). Rather than including an activation button (126) for activating transducer (112), however, transducer (112) is activated by pivoting trigger (128) relative to pistol grip (124). In some examples, instrument (710) may also include an activation button (126), in addition to the trigger activation features described below.

Figure 11A:
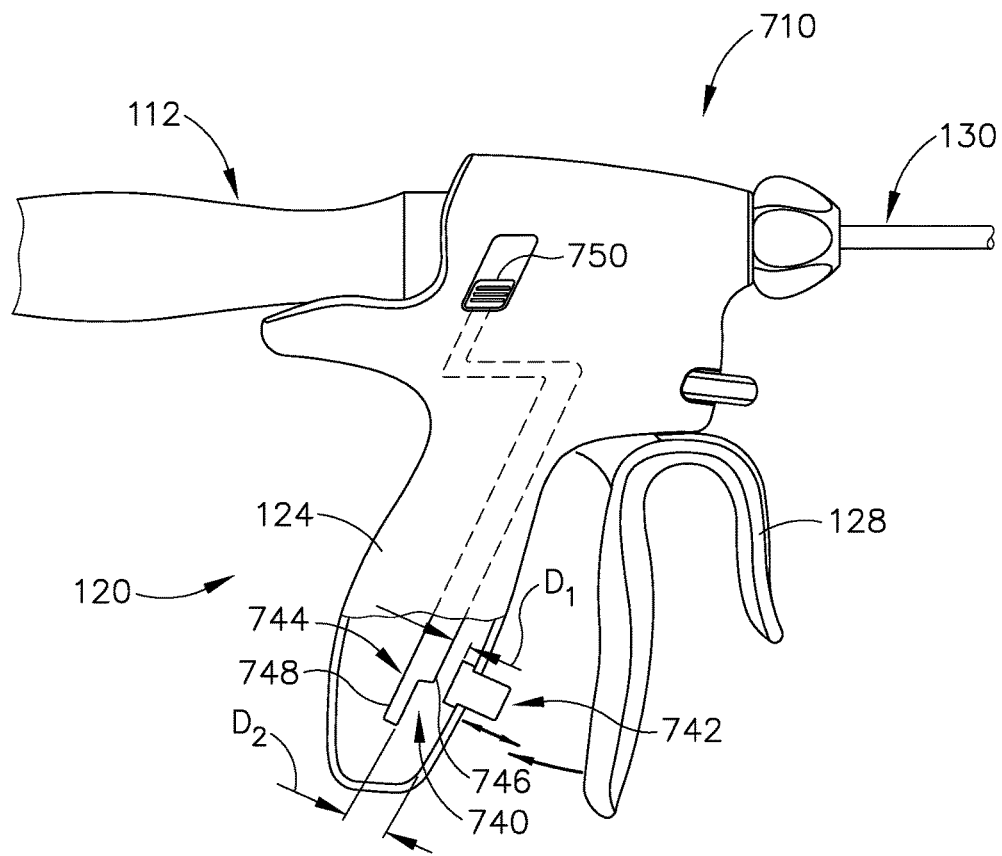
FIG. 11A depicts a side elevational view of an exemplary surgical instrument, showing a trigger blocking mechanism in a first position and a trigger in a non-actuated position.
Figure 12A:
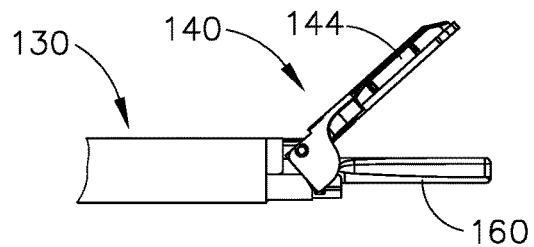
FIG. 12A depicts an end effector of the instrument of FIG. 11A, showing the end effector in an open configuration, associated with the non-actuated position of the trigger shown in FIG. 11A.
Figure 11B:
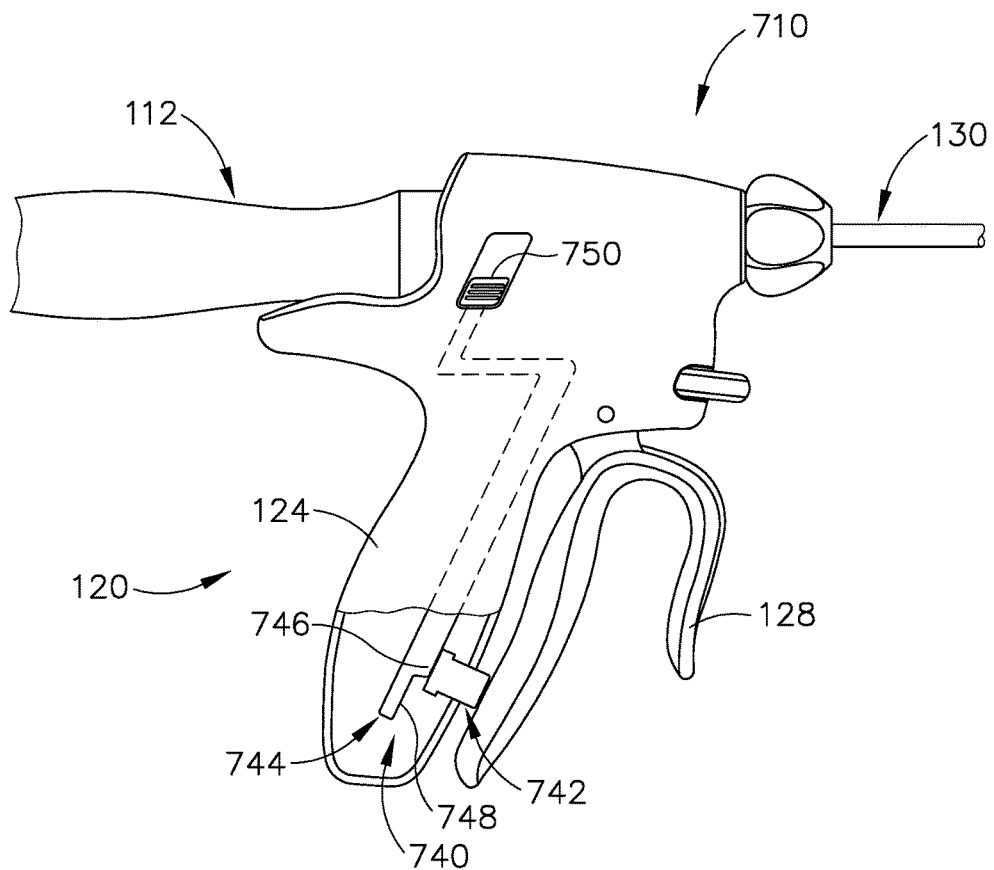
FIG. 11B depicts a side elevational view of the instrument of FIG. 11A, showing the trigger blocking mechanism in the first position and the trigger in a first actuated position.
Figure 11C:
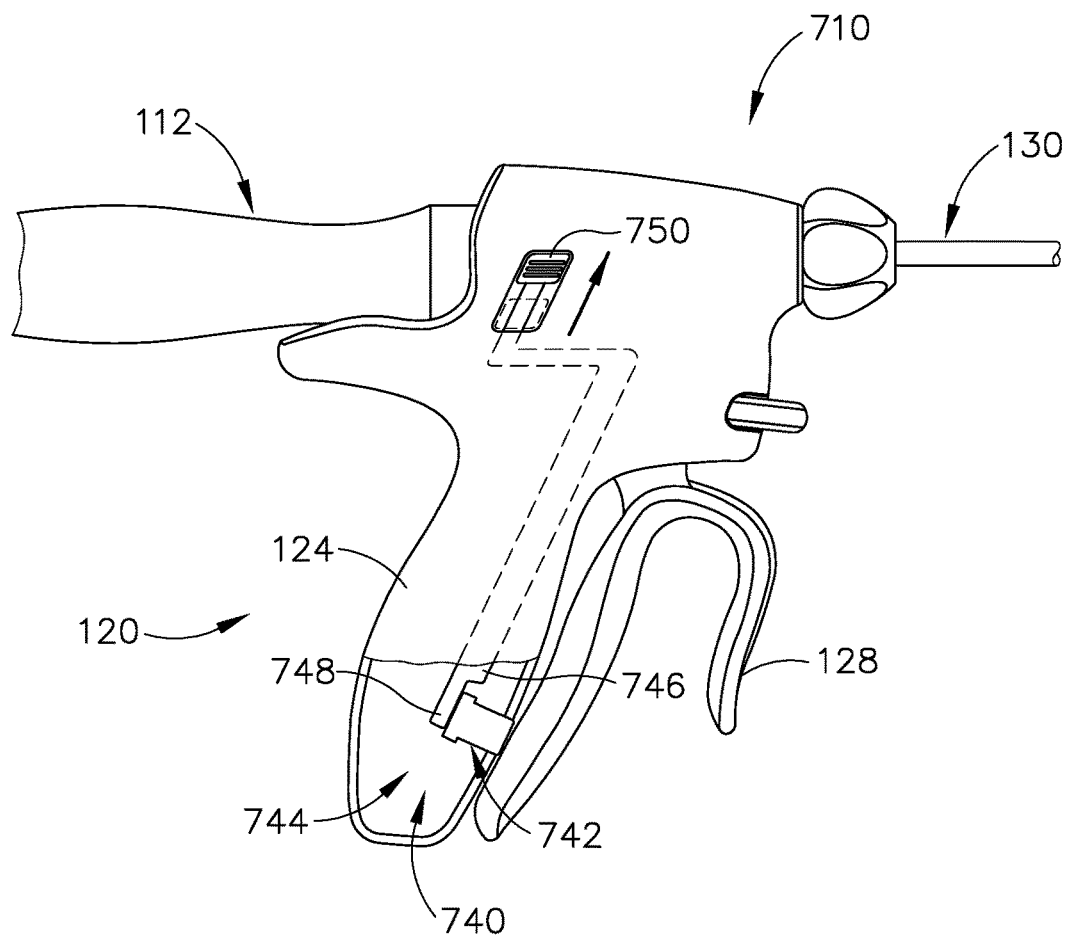
FIG. 11C depicts a side elevational view of the instrument of FIG. 11A, showing the trigger blocking mechanism in a second position and the trigger in a second actuated position.

As shown in FIGS. 11A-11C, handle assembly (120) includes a stop assembly (740) that is movable between a first position and a second position. Stop assembly (740) comprises a first stop member (742) and a second stop member (744). A button (750) protrudes proximally from the upper end of second stop member (744). Button (750) is exposed through the proximal end of handle assembly (120) such that an operator may engage button with the thumb of the hand grasping pistol grip (124) to slide button (750) upwardly and downwardly between the positions shown in FIGS. 11A-11C. First stop member (742) is positioned on a distal portion of pistol grip (124) and is movable proximally within pistol grip (124) in response to being contacted by trigger (128), depending on the position of second stop member (742). Second stop member (744) includes a first portion (746) that is spaced from first stop member (742) a first distance ($D_1$), and a second portion (748) that is spaced from first stop member (742) a second distance ($D_2$). In the present example, the first distance ($D_1$) is shorter than the second distance ($D_2$).

Figure 12B:
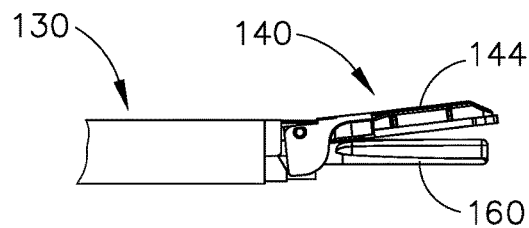
FIG. 12B depicts the end effector of FIG. 12A in a partially closed configuration, associated with a first actuated position of the trigger shown in FIG. 11B.

Second stop member (744) is movable generally along the axis of pistol grip (124). Particularly, second stop member (744) is movable from a first position where first stop member (742) is coincident with the first portion (746) as shown in FIGS. 11A-11B; and a second position where first stop member (742) is coincident with second portion (748)

as shown in FIG. 11C. When second stop member (744) is in the first position as shown in FIGS. 11A-11B, stop assembly (740) restricts pivotal movement of trigger (128) toward pistol grip (124). In particular, trigger (128) abuts first stop member (742), which abuts first portion (746) to provide a hard stop. Stop assembly (740) thus only allows trigger (128) to move from a non-actuated position (FIG. 11A) to a partially actuated position (FIG. 11B) when second stop member is in the first position. This restricted pivotal movement of trigger (128) results in clamp arm (144) only pivoting from an open position (FIG. 12A) to a partially closed position (FIG. 12B). With clamp arm (144) only being capable of partially closing in this mode of operation, end effector (140) is only capable of providing a relatively low degree of compression to tissue. Thus, end effector (140) will seal tissue but not cut the tissue when blade (160) is activated while clamp arm (144) partially compresses the tissue against blade (160) in the partially closed position as shown in FIG. 12B. In some variations, clamp arm (144) is theoretically capable of contacting blade (160) in this state, but a force limiting mechanism in handle assembly (120) restricts the compression force that may be achieved between clamp arm (144) and blade (160). Various suitable forms that such a force limiting mechanism may take will be apparent to those of ordinary skill in the art in view of the teachings herein.

Figure 12C:
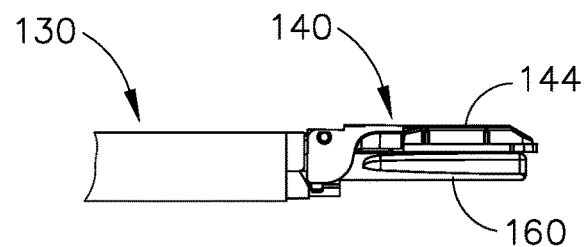
FIG. 12C depicts the end effector of FIG. 12A in a closed configuration, associated with a second actuated position of the trigger shown in FIG. 11C.

When second stop member (744) is in the second position as shown in FIG. 11C, stop assembly (740) no longer restricts pivotal movement of trigger (128) toward pistol grip (124). In particular, second portion (748) is positioned to provide clearance for stop member (742) to move proximally in pistol grip (124) when second stop member (744) is in the second position. Thus, as trigger (128) is pivoted toward pistol grip (124), trigger (128) eventually engages second stop member (744) and drives stop member (744) into pistol grip (124) as trigger (128) reaches the fully actuated position shown in FIG. 12C. This unobstructed pivotal movement of trigger (128) allows clamp arm (144) pivoting fully from the open position (FIG. 12A) to the fully closed position (FIG. 12C). With clamp arm (144) being capable of fully closing in this mode of operation, end effector (140) is capable of providing a relatively high degree of compression to tissue. Thus, end effector (140) will cut and seal tissue when blade (160) is activated while clamp arm (144) fully compresses the tissue against blade (160) in the fully closed position as shown in FIG. 12C.

In the present example, first stop member (742) provides a switch that activates transducer (112) and blade (160) in response to engagement of first stop member (742) by trigger (128). Thus, when trigger (128) is in the partially actuated position (FIG. 11B) or the fully actuated position (FIG. 11C), transducer (112) and blade (160) are activated. In some versions, the power level at which transducer (112) and blade (160) are activated is the same regardless of whether trigger (128) is in the partially actuated position (FIG. 11B) or the fully actuated position (FIG. 11C). In such versions, the variation in tissue effects is provided by the variation in the degree of closure of clamp arm (144) as shown in FIGS. 12B and 12C. In some other versions, the power level at which transducer (112) and blade (160) are activated will also vary based on whether trigger (128) is in the partially actuated position (FIG. 11B) or the fully actuated position (FIG. 11C). For instance, transducer (112) and blade (160) may be activated at a relatively low power level in the state shown in FIG. 11B; and at a relatively high power level in the state shown in FIG. 11C. Various suitable ways in which a switch or switches may be incorporated into first stop member (742) will be apparent to those of ordinary skill in the art in view of the teachings herein.

It should also be understood that switches may be incorporated into second stop member (744) to activate transducer (112) and blade (160) in response to pivotal movement of trigger (128). For instance, a first switch may be incorporated into first portion (746), such that first stop member (742) actuates the first switch in the state shown in FIG. 11B. Similarly, a second switch may be incorporated into second portion (748), such that first stop member (742) actuates the second switch in the state shown in FIG. 11C. Additionally or alternatively, instrument (710) may include a sensor that senses the angle (or other characteristic(s)) of trigger (128) relative to particular components of instrument (710), such as, for example, pistol grip (124). Such a sensor may act as a switch that activates transducer (112) and blade (160) in response to pivotal movement of trigger (128).

Figure 13A:
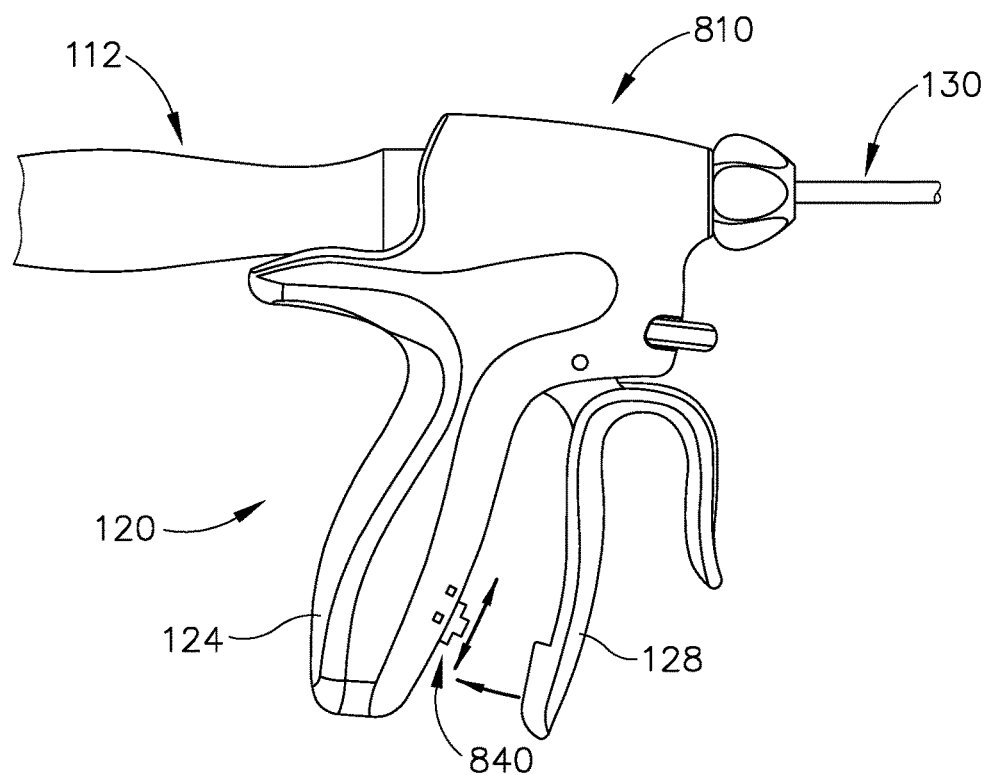
FIG. 13A depicts a side elevational view of another exemplary surgical instrument, showing an exemplary alternative blocking mechanism in a first position and a trigger in a non-actuated position.
Figure 13B:
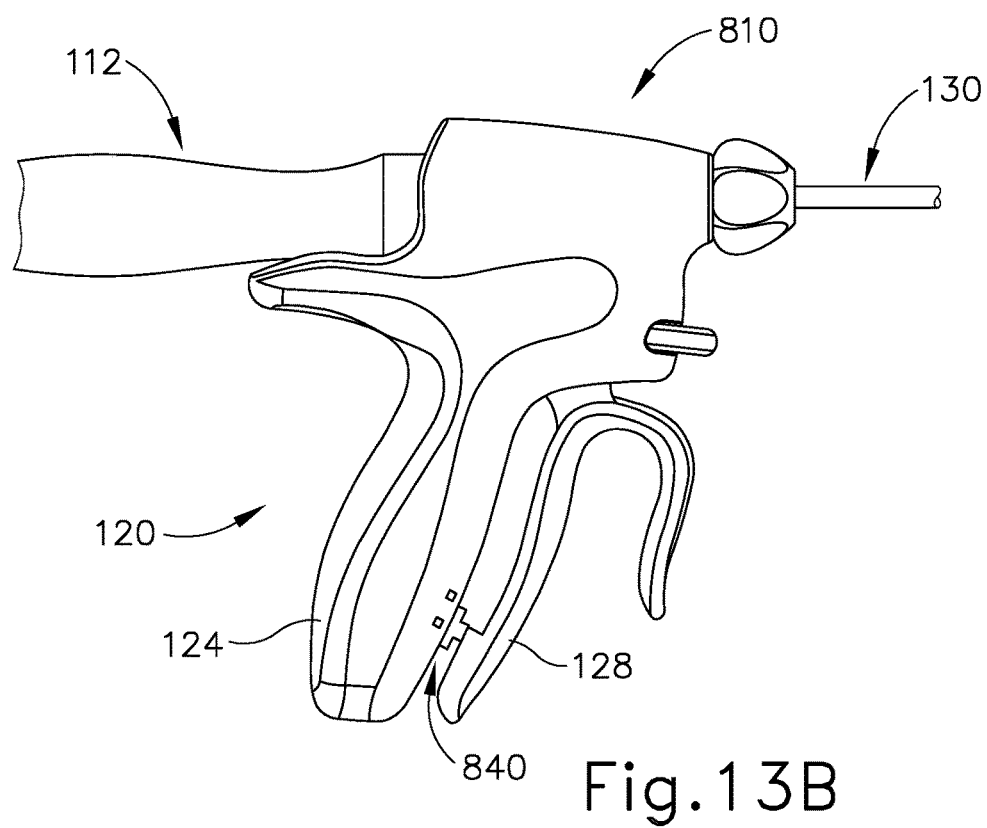
FIG. 13B depicts a side elevational view of the surgical instrument of FIG. 13A, showing the blocking mechanism in the first position and the trigger in a first actuated position.
Figure 13C:
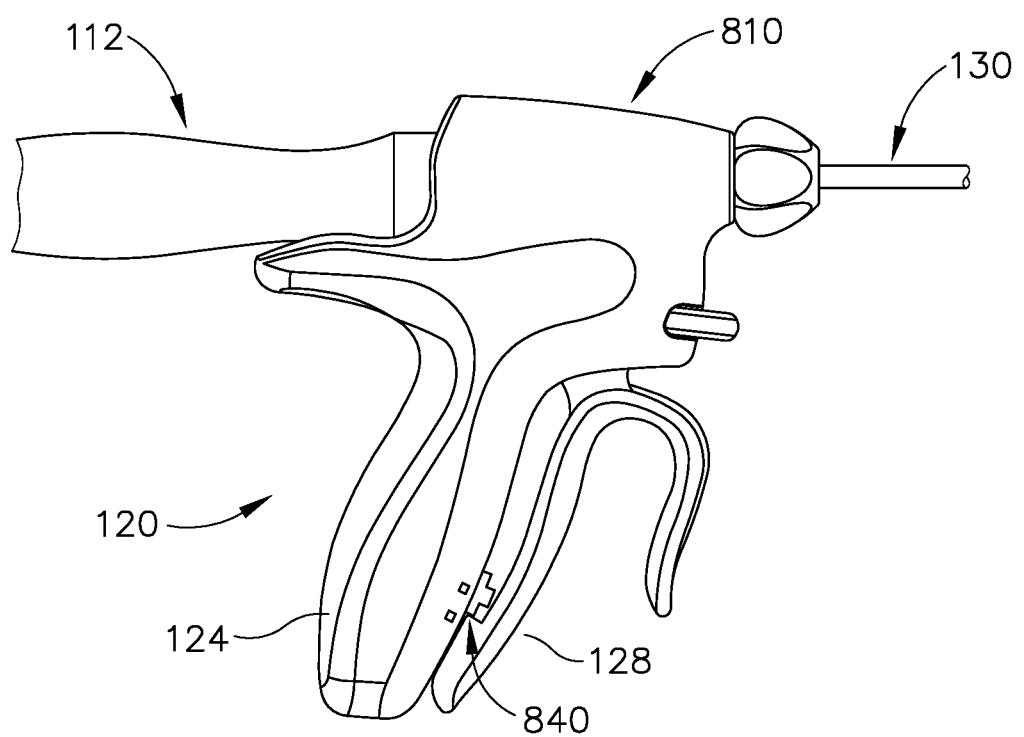
FIG. 13C depicts a side elevational view of the surgical instrument of FIG. 13A, showing the blocking mechanism in a second position and the trigger in a second actuated position.

FIGS. 13A-13C show an exemplary alternative surgical instrument (810) that is also configured to be activated by pivoting trigger (128) relative to pistol grip (124). Instrument (810) of this example is configured to operate substantially similar to surgical instrument (110, 710). Therefore, identical or similar structures are labeled with like reference numerals without further explanation below. It will be further understood that transducer (112) may be in communication with a generator (12, 116) via cable (14). As shown, instrument (810) includes an alternative stop member that is slidable along pistol grip (124) between a first position (FIGS. 13A-13B) and a second position (FIG. 13C). As shown in FIG. 13B, in the first position, stop member (840) allows trigger (128) to pivot relative to pistol grip (124) a first distance to only a partially actuated position. Stop member (840) in the first position provides an obstruction that prevents trigger (128) from pivoting further than the partially actuated position. However, when stop member (840) is in the second position, stop member (840) allows trigger (128) to pivot relative to pistol grip (124) to a fully actuated position. It should be understood that the partial or full actuation of trigger (128) will result in the partial or full closure of clamp arm (144) relative to blade (160), as described above with respect to FIGS. 12A-12C. Thus, when stop member (840) is in the first position as shown in FIGS. 13A-13B, stop member (840) provides instrument (810) in a "seal only" mode. When stop member (840) is in the second position as shown in FIG. 13C, stop member (840) provides instrument (810) in a "seal and cut" mode.

Stop member (840) may also include one or more switches that activate transducer (112) and blade (160) in response to engagement of stop member (840) by trigger (128). Thus, when trigger (128) is in the partially actuated position (FIG. 13B) or the fully actuated position (FIG. 13C), transducer (112) and blade (160) are activated. In some versions, the power level at which transducer (112) and blade (160) are activated is the same regardless of whether trigger (128) is in the partially actuated position (FIG. 13B) or the fully actuated position (FIG. 13C). In such versions, the variation in tissue effects is provided by the variation in the degree of closure of clamp arm (144) as described above with respect to FIGS. 12B and 12C. In some other versions, the power level at which transducer (112) and blade (160) are activated will also vary based on whether trigger (128) is in the partially actuated position (FIG. 13B) or the fully actuated position (FIG. 13C). For instance, transducer (112) and blade (160) may be activated at a relatively low power level in the state shown in FIG. 13B; and at a relatively high power level in the state shown in FIG. 13C. Various suitable ways in which a switch or switches may be incorporated into stop member (840) will be apparent to those of ordinary skill in the art in view of the teachings herein.

FIG. 14 shows features of a handle assembly (120) of another exemplary alternative instrument (910) that is also configured to be activated by pivoting trigger (128) relative to pistol grip (124). Instrument (910) of this example is configured to operate substantially similar to surgical instrument (110, 710, 810). Therefore, identical or similar structures are labeled with like reference numerals without further explanation below. It will be further understood that instrument (910) includes a transducer (112) that may be in communication with a generator (12, 116) via cable (14). As shown, instrument (810) includes an alternative stop member (940) that is slidable along pistol grip (124) among first, second and third positions in response to user actuating slider (941). In this example, trigger (128) includes a contact portion (942) internal to pistol grip (124). Contact portion (942) is configured to contact one of three portions of stop member (940) in order to pivot among first, second, and third pivoted positions. Particularly, trigger (128) may pivot such that contact portion (942) contacts first portion (944) when stop member (940) is in a first position. Similarly, trigger (128) may pivot such that contact portion (942) contacts second portion (946) when stop member (940) is in a second position. Further, trigger (128) may pivot such that contact portion (942) contacts third portion (944) when stop member (940) is in a third position.

It should be understood that portions (944, 946, 948) may restrict actuation of trigger (128) to varying degrees, depending on which portion (944, 946, 948) is positioned to engage contact portion (942) based on the position of stop member (940) within pistol grip (124). It should also be understood that the restriction of actuation of trigger (128) will further result in restriction of the closure of clamp arm (144) as described above with respect to FIGS. 12A-12C. Thus, stop member (940) is operable to vary the compression that may be applied to tissue by end effector (140), thereby providing different modes of operation such as a "seal only" mode and a "seal and cut" mode.

Stop member (940) may also include one or more switches that activate transducer (112) and blade (160) in response to engagement of stop member (940) by trigger (128). Thus, when trigger (128) is in a partially actuated position (e.g., engaging portion (944) or portion (946)) or the fully actuated position (e.g., engaging portion (948)), transducer (112) and blade (160) are activated. In some versions, the power level at which transducer (112) and blade (160) are activated is the same regardless of whether trigger (128) is in a partially actuated position or the fully actuated position. In such versions, the variation in tissue effects is provided by the variation in the degree of closure of clamp arm (144) as described above with respect to FIGS. 12B and 12C. In some other versions, the power level at which transducer (112) and blade (160) are activated will also vary based on whether trigger (128) is in a partially actuated position or the fully actuated position. For instance, transducer (112) and blade (160) may be activated at a relatively low power level when trigger (128) engages portion (946); and at a relatively high power level when trigger (128) engages portion (948). Various suitable ways in which a switch or switches may be incorporated into stop member (940) will be apparent to those of ordinary skill in the art in view of the teachings herein.

V. Surgical Instrument with Continuously Variable Activation Button

Figure 15:
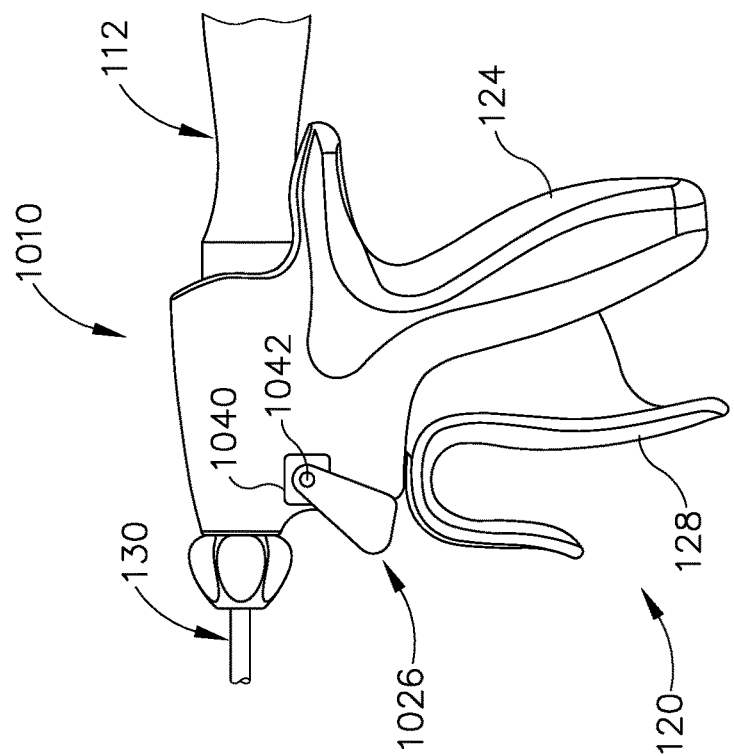
FIG. 15 depicts a side elevational view of an exemplary alternative handle assembly of another exemplary surgical instrument, with a pivoting trigger coupled directly with a potentiometer.

FIG. 15 shows an exemplary alternative surgical instrument (1010) that is configured to operate substantially similar to surgical instrument (110). Therefore, identical or similar structures are labeled with like reference numerals without further explanation below. It will be understood that although an end effector is not shown in FIG. 15, instrument (1010) includes an end effector just like end effector (140). It will be further understood that transducer (112) may be in communication with a generator (12, 116) via cable (14). As shown, surgical instrument (1010) includes a rotatable activation button (1026) that is directly coupled with a potentiometer (1040). In particular, button (1026) is pivotably coupled with potentiometer (1040) via a pin (1042) that passes through the center of potentiometer (1040). Pin (1042) is fixedly secured to button (1026) such that pin (1042) rotates as button (1026) pivots. Pin (1042) is also secured to the rotating contact in potentiometer (1040), such that the resistance value of potentiometer (1040) changes in direct proportion to the pivotal movement of button (1026). This variable resistance provided through potentiometer (1040) provides a varied power output through transducer (112) and blade (160). In other words, the ultrasonic power applied to tissue via end effector (140) will vary based on the pivotal position and/or rate of change in position of button (1026). In some alternative versions, potentiometer (1040) is replaced with an encoder assembly that is operable to track the pivotal position of button (1026). Data from the encoder assembly may thus be used to provide a varied power output through transducer (112) and blade (160).

Figure 16:
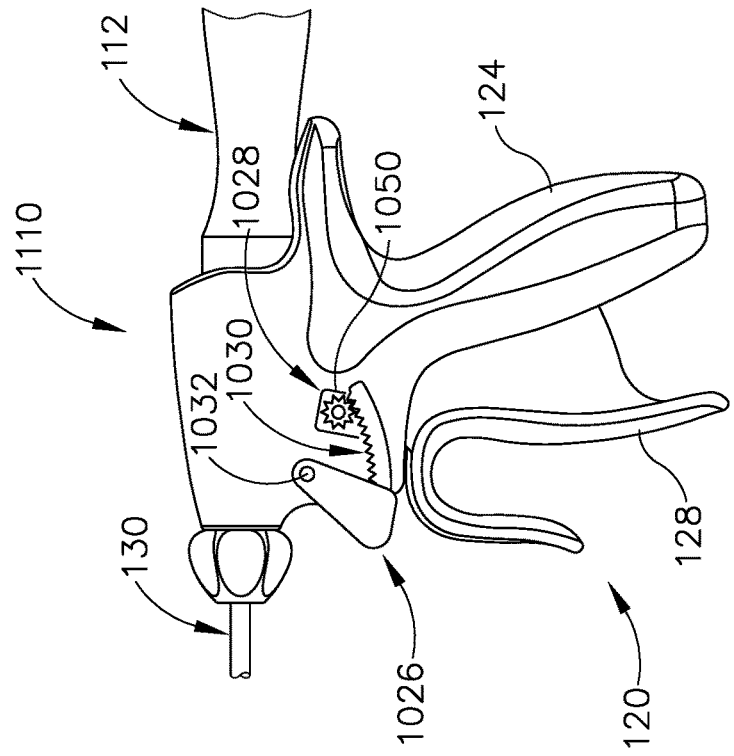
FIG. 16 depicts a side elevational view of an exemplary alternative handle assembly of another exemplary surgical instrument, with a pivoting trigger coupled with a potentiometer via a rack and pinion assembly.

FIG. 16 shows a merely illustrative variation of the configuration shown in FIG. 15. In particular, FIG. 16 shows a configuration where a curved rack (1030) is unitarily secured to button (1026). Curved rack (1030) is engaged with a pinion (1028), which is directly coupled with a potentiometer (1050). Thus, as button (1026) pivots about a pin (1032), curved rack (1030) causes pinion (1028) to rotate, which in turn changes the resistance value of potentiometer (1050). This variable resistance provided through potentiometer (1050) provides a varied power output through transducer (112) and blade (160). In other words, the ultrasonic power applied to tissue via end effector (140) will vary based on the pivotal position (and/or rate of change in position) of button (1026). Unlike the configuration shown in FIG. 15, the configuration shown in FIG. 16 will provide a greater change in the resistance value of potentiometer (1050) in response to pivotal movement of trigger (1026), due to the presence of curved rack (1030) and pinion (1028). In other words, the configuration shown in FIG. 16 will provide greater sensitivity to pivotal movement of trigger (1026) than the configuration shown in FIG. 15. Still other suitable configurations will be apparent to those of ordinary skill in the art in view of the teachings herein.

In both of the examples shown in FIGS. 15-16, as button (1026) is pivoted proximally, a continuously variable power level is provided, rather than operating in discrete modes or power levels. Particularly, in the example shown, as the angular displacement of proximal actuation of button (1026) increases, the power level of transducer (112) and blade (160) increases. Other suitable relationships between the power setting or displacement of ultrasonic blade (160) and the depth or pressure of button (1026) will be apparent to persons skilled in the art in view of the teachings herein. In some examples, the tension or physical resistance of button (1026) may be varied across the throw (i.e., across the range of pivotal movement of button (1026)) in order to provide the operator with tactile feedback and more control over the movement of button (1026) and the ultrasonic blade (160). Providing button (1026) with a continuously variable power level enables the operator to operate across a continuum of modes (e.g., power levels) without being constrained to discrete settings (maximum, minimum, etc.).

In some other variations, as button (1026) is pivoted proximally, the power level is progressively increased in a step-wise fashion through a finite number of discrete power levels. In other words, the power level need not necessarily be continuously variable in all versions that incorporate button (1026).

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic instrument comprising: (a) a body; (b) an actuation assembly, wherein the actuation assembly comprises a mode selection member and an activation member; (c) a shaft assembly extending distally from the body, wherein the shaft assembly comprises an acoustic waveguide; and (d) an end effector comprising an ultrasonic blade, wherein the ultrasonic blade is in acoustic communication with the acoustic waveguide, wherein the end effector is configured to be activated in a first activation mode in response to actuation of the activation member when the mode selection member is in a first position, wherein the end effector is configured to be activated in a second activation mode in response to actuation of the activation member when the mode selection member is in a second position.

Example 2

The ultrasonic instrument of Example 1, wherein the mode selection member comprises a sensor.

Example 3

The ultrasonic instrument of Example 2, wherein the sensor is configured to sense an orientation of the body and thereby provide a mode selection based on the orientation of the body.

Example 4

The ultrasonic instrument of Example 3, wherein the sensor comprises an accelerometer.

Example 5

The ultrasonic instrument of any one or more of Examples 1 through 4, wherein the mode selection member comprises a slidable member.

Example 6

The ultrasonic instrument of Example 5, further comprising a potentiometer, wherein the potentiometer is in communication with the slidable member.

Example 7

The ultrasonic instrument of any one or more of Examples 1 through 6, wherein the mode selection member comprises a toggle button.

Example 8

The ultrasonic instrument of any one or more of Examples 1 through 7, wherein the mode selection member comprises a rotary dial.

Example 9

The ultrasonic instrument of any one or more of Examples 1 through 8, wherein the mode selection member is movable among a plurality of positions, wherein each of the plurality of positions is associated with a respective discrete operating mode.

Example 10

The ultrasonic instrument of any one or more of Examples 1 through 9, further comprising a trigger, wherein the end effector further comprises a clamp arm, wherein the clamp arm is configured to pivot relative to the ultrasonic blade in response to actuation of the trigger in order to clamp tissue between the clamp arm and the ultrasonic blade.

Example 11

The ultrasonic instrument of Example 10, wherein the activation member comprises the trigger.

Example 12

The ultrasonic instrument of Example 11, wherein the mode selection member comprises a blocking member configured to selectively restrict actuation of the trigger.

Example 13

The ultrasonic instrument of Example 12, wherein the blocking member is movable from a first position to a second position, wherein the clamp arm is configured to pivot relative to the ultrasonic blade to a partially closed position in response to actuation of the trigger when the blocking member is in the first position, wherein the clamp arm is configured to pivot relative to the ultrasonic blade to a fully closed position in response to actuation of the trigger when the blocking member is in the second position.

Example 14

The ultrasonic instrument of any one or more of Examples 1 through 13, wherein the mode selection member comprises a plurality of switches, wherein the plurality of switches are positioned on a single button.

Example 15

The ultrasonic instrument of any one or more of Examples 1 through 14, wherein the body comprises a grip portion configured to be grasped by a hand of an operator, wherein the mode selection member is located proximate to the grip portion such that the mode selection member is positioned to be accessible by a thumb of a hand grasping the grip portion.

Example 16

The ultrasonic instrument of any one or more of Examples 1 through 15, wherein the activation member comprises a button on a distal portion of the body.

Example 17

An ultrasonic instrument comprising: (a) a body; (b) an actuation assembly, wherein the actuation assembly comprises a mode selection member and an activation member; (c) a shaft assembly extending distally from the body, wherein the shaft assembly comprises an acoustic waveguide; and (d) an end effector comprising an ultrasonic blade, wherein the ultrasonic blade is in acoustic communication with the acoustic waveguide, wherein the end effector is configured to be activated in a first activation mode in response to actuation of the activation member when the mode selection member is in a first position, wherein the end effector is configured to be activated in a plurality of operation modes according to different positions of the mode selection member and in response to actuation of the activation member.

Example 18

The ultrasonic instrument of Example 17, wherein the body comprises a handle assembly, wherein the handle assembly comprises a pistol grip, wherein the mode selection member is positioned on or near the pistol grip such that the mode selection member is accessible by a hand grasping the pistol grip.

Example 19

An ultrasonic instrument comprising: (a) a body; (b) a trigger pivotably coupled with the body; (c) a shaft assembly extending distally from the body, wherein the shaft assembly comprises an acoustic waveguide; (d) an end effector comprising: (i) an ultrasonic blade, wherein the ultrasonic blade is in acoustic communication with the acoustic waveguide, and (ii) a clamp arm, wherein the clamp arm is configured to pivot toward and away from the ultrasonic blade in response to pivotal movement of the trigger relative to the body; and (e) a trigger blocking member movably coupled with the body, wherein the trigger blocking member is movable between a first position and a second position, wherein the trigger blocking member is configured to permit the trigger to pivot from a non-actuated position to only a partially actuated position when the trigger blocking member is in the first position, thereby restricting movement and/or clamping force of the clamp arm, wherein the trigger blocking member is configured to permit the trigger to pivot from the non-actuated position to a fully actuated position when the trigger blocking member is in the second position, wherein the trigger blocking member is configured to prevent the trigger from pivoting from the partially actuated position to the fully actuated position when the trigger blocking member is in the first position.

Example 20

The ultrasonic instrument of Example 19, wherein the body comprises a pistol grip, wherein the trigger is pivotable toward and away from the pistol grip, wherein the trigger blocking member is slidably disposed in the pistol grip.

Example 21

An ultrasonic instrument comprising: (a) a body; (b) an actuation assembly, wherein the actuation assembly comprises an activation member, wherein the activation member is configured to move relative to the body; (c) a shaft assembly extending distally from the body, wherein the shaft assembly comprises an acoustic waveguide; and (d) an end effector comprising an ultrasonic blade, wherein the ultrasonic blade is in acoustic communication with the acoustic waveguide, wherein the end effector is configured to be activated in response to movement of the activation member relative to the body at a power level that is selected based on the position of the activation member relative to the body such that the activation member is operable to activate the end effector at a first power level when the activation member is at a first position relative to the body and such that the activation member is operable to activate the end effector at a second power level when the activation member is at a second position relative to the body.

Example 22

The ultrasonic instrument of Example 21, wherein the activation member is operable to activate the end effector through a continuously variable range of power levels based on the position of the activation member relative to the body.

Example 23

The ultrasonic instrument of Example 21, wherein the activation member is operable to activate the end effector through a range of discrete power levels based on the position of the activation member relative to the body.

VII. Miscellaneous

As used herein, the term "activation mode" should be understood to include various different meanings. For instance, one activation mode may provide ultrasonic power via an ultrasonic blade at one power level while another activation mode may provide ultrasonic power via an ultrasonic blade at another power level. As another example, one activation mode may provide ultrasonic power via an ultrasonic blade with one power profile (e.g., power varying as a function of time and/or some other variable(s)) while another activation mode may provide ultrasonic power via an ultrasonic blade at another power profile (e.g., power varying as a different function of time and/or some other variable(s)). As another example, one power level may provide one closed clamp arm position and/or clamping force while another power level may provide another closed clamp arm position and/or clamping force. Other different kinds of activation modes will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic instrument comprising:
   (a) a body;
   (b) an actuation assembly, wherein the actuation assembly comprises a mode selection member and an activation member, wherein the mode selection member is configured to actuate relative to the body between a first position, and a second position;
   (c) a shaft assembly extending distally from the body, wherein the shaft assembly comprises an acoustic waveguide;
   (d) an end effector comprising an ultrasonic blade, wherein the ultrasonic blade is in acoustic communication with the acoustic waveguide, wherein the end effector is configured to be activated in a first activation mode in response to actuation of the activation member when the mode selection member is in the first position, wherein the end effector is configured to cut and seal tissue in the first activation mode, wherein the end effector is configured to be activated in a second activation mode in response to actuation of the activation member when the mode selection member is in the second position, wherein the end effector is configured to only seal tissue without severing tissue in the second activation mode; and
   (e) a display configured to display a readout based on the position of the mode selection member relative to the body.

2. The ultrasonic instrument of claim 1, wherein the mode selection member comprises a sensor.

3. The ultrasonic instrument of claim 2, wherein the sensor is configured to sense an orientation of the body and thereby provide a mode selection based on the orientation of the body.

4. The ultrasonic instrument of claim 3, wherein the sensor comprises an accelerometer.

5. The ultrasonic instrument of claim 1, wherein the mode selection member comprises a slidable member.

6. The ultrasonic instrument of claim 5, further comprising a potentiometer, wherein the potentiometer is in communication with the slidable member.

7. The ultrasonic instrument of claim 1, wherein the mode selection member comprises a toggle button.

8. The ultrasonic instrument of claim 1, wherein the mode selection member comprises a rotary dial.

9. The ultrasonic instrument of claim 1, wherein the mode selection member is movable among a plurality of positions, wherein each of the plurality of positions is associated with a respective discrete operating mode.

10. The ultrasonic instrument of claim 1, further comprising a trigger, wherein the end effector further comprises a clamp arm, wherein the clamp arm is configured to pivot relative to the ultrasonic blade in response to actuation of the trigger in order to clamp tissue between the clamp arm and the ultrasonic blade.

11. The ultrasonic instrument of claim 10, wherein the activation member comprises the trigger.

12. The ultrasonic instrument of claim 11, wherein the mode selection member comprises a blocking member configured to selectively restrict actuation of the trigger.

13. The ultrasonic instrument of claim 12, wherein the blocking member is movable from a first position to a second position, wherein the clamp arm is configured to pivot relative to the ultrasonic blade to a partially closed position in response to actuation of the trigger when the blocking member is in the first position, wherein the clamp arm is configured to pivot relative to the ultrasonic blade to a fully closed position in response to actuation of the trigger when the blocking member is in the second position.

14. The ultrasonic instrument of claim 1, wherein the mode selection member comprises a plurality of switches, wherein the plurality of switches are positioned on a single button.

15. The ultrasonic instrument of claim 1, wherein the body comprises a grip portion configured to be grasped by a hand of an operator, wherein the mode selection member is located proximate to the grip portion such that the mode selection member is positioned to be accessible by a thumb of a hand grasping the grip portion.

16. The ultrasonic instrument of claim 1, wherein the activation member comprises a button on a distal portion of the body.

17. An ultrasonic instrument comprising:
(a) a body;
(b) an actuation assembly, wherein the actuation assembly comprises a mode selection member and an activation member, wherein the mode selection member is configured to actuate relative to the body between a first position and a second position;
(c) a shaft assembly extending distally from the body, wherein the shaft assembly comprises an acoustic waveguide;
(d) an end effector comprising an ultrasonic blade, wherein the ultrasonic blade is in acoustic communication with the acoustic waveguide, wherein the ultrasonic blade is configured to be activated in a first power level in response to actuation of the activation member when the mode selection member is in the first position, wherein the ultrasonic blade is configured to be activated in a plurality of power levels according to different positions of the mode selection member between the first position and the second position in response to actuation of the activation member; and
(e) a display configured to display a readout based on the position of the mode selection member relative to the body.

18. The ultrasonic instrument of claim 17, wherein the body comprises a handle assembly, wherein the handle assembly comprises a pistol grip, wherein the mode selection member is positioned on or near the pistol grip such that the mode selection member is accessible by a hand grasping the pistol grip.

19. An ultrasonic instrument comprising:
(a) a body;
(b) an actuation assembly, wherein the actuation assembly comprises a mode selection member and an activation member, wherein the mode selection member is configured to linearly translate relative to the body between a first position and a second position;
(c) a shaft assembly extending distally from the body, wherein the shaft assembly comprises an acoustic waveguide;
(d) an end effector comprising an ultrasonic blade, wherein the ultrasonic blade is in acoustic communication with the acoustic waveguide, wherein the ultrasonic blade is configured to be activated in a first energy level in response to actuation of the activation member when the mode selection member is in the first position, wherein the ultrasonic blade is configured to be activated in a plurality of energy levels according to different positions of the mode selection member between the first position and the second position and in response to actuation of the activation member; and
(e) a display configured to show a readout based on the position of the mode selection member relative to the body.

20. An ultrasonic instrument comprising:
(a) a body;
(b) an actuation assembly, wherein the actuation assembly comprises a mode selection member and an activation member, wherein the mode selection member is configured to linearly translate relative to the body between a first position and a second position;
(c) a shaft assembly extending distally from the body, wherein the shaft assembly comprises an acoustic waveguide;
(d) an end effector comprising an ultrasonic blade, wherein the ultrasonic blade is in acoustic communication with the acoustic waveguide, wherein the ultrasonic blade is configured to be activated across a continuum of power levels in response to actuation of the activation member based on a location of the mode selection member between the first position and the second position; and
(e) a display configured to display a readout based on the location of the mode selection member relative to the body.

21. The ultrasonic instrument of claim 20, wherein the shaft assembly defines a longitudinal axis, wherein the mode selection member is configured to linearly translate along a distance parallel to the longitudinal axis.

* * * * *